(12) United States Patent
Amat Girbau et al.

(10) Patent No.: US 8,955,999 B2
(45) Date of Patent: Feb. 17, 2015

(54) LAMP AND PLENUM FOR LAMINAR AIR FLOW CEILING

(75) Inventors: Josep Amat Girbau, Barcelona (ES); Alicia Casals Gelpi, Sant Just Desvern (ES); Enric Laporte Rosello, Sabadell (ES)

(73) Assignees: Corporacio Sanitaria Parc Tauli, Sabadell (ES); Azbil Telstar Technologies, S.L., Terrassa (ES); Fundacio Institut de Bioenginyeria de Catalunya, Barcelona (ES)

( * ) Notice: Subject to any disclaimer, the term of this patent is extended or adjusted under 35 U.S.C. 154(b) by 0 days.

(21) Appl. No.: 13/812,811

(22) PCT Filed: Jul. 28, 2011

(86) PCT No.: PCT/EP2011/062998
§ 371 (c)(1),
(2), (4) Date: Apr. 5, 2013

(87) PCT Pub. No.: WO2012/013749
PCT Pub. Date: Feb. 2, 2012

(65) Prior Publication Data
US 2013/0182417 A1    Jul. 18, 2013

(30) Foreign Application Priority Data
Jul. 28, 2010   (EP) .................... 10171132

(51) Int. Cl.
*F21V 21/03*    (2006.01)
*A61B 19/00*    (2006.01)
(Continued)

(52) U.S. Cl.
CPC ............ *F21V 21/03* (2013.01); *A61B 19/5202* (2013.01); *A61G 13/108* (2013.01);
(Continued)

(58) Field of Classification Search
CPC ........ F24F 3/161; H02K 21/025; B01D 46/10
USPC .......................... 362/147, 145, 241
See application file for complete search history.

(56) References Cited

U.S. PATENT DOCUMENTS 3,967,107 A    6/1976    Junginger et al.
5,504,665 A    4/1996    Osteen et al.
(Continued)

FOREIGN PATENT DOCUMENTS

DE        3133951 A1     1/1983
DE    102005036275 A1     2/2007
(Continued)

OTHER PUBLICATIONS

International Search Report and Written Opinion of the International Searching Authority, Search Report, Application No. PCT/EP2011/062998 issued by the European Patent Office, Rijswijk, Netherlands, dated Feb. 22, 2012.
(Continued)

*Primary Examiner* — Tracie Y Green
(74) *Attorney, Agent, or Firm* — Peter B. Scull; Hamilton DeSanctis & Cha LLP

(57) ABSTRACT

A lamp having a first module for being attached to a ceiling or wall element, a second module connected to the first module and being rotatable with respect to the first module along a first axis, a third module having one or more light-emitting elements, the third module being connected to the second module and rotatable with respect to the second module along a second axis, the second axis being substantially perpendicular to the first axis.

12 Claims, 7 Drawing Sheets

(51) Int. Cl.

| | | |
|---|---|---|
| *A61G 13/10* | (2006.01) | |
| *E04B 9/00* | (2006.01) | |
| *E04B 9/02* | (2006.01) | |
| *F21S 2/00* | (2006.01) | |
| *F21S 8/02* | (2006.01) | |
| *F21S 8/00* | (2006.01) | |
| *F21V 21/02* | (2006.01) | |
| *F21V 21/15* | (2006.01) | |
| *F21V 21/30* | (2006.01) | |
| *F21V 33/00* | (2006.01) | |
| *H05B 33/08* | (2006.01) | |
| *H05B 37/02* | (2006.01) | |
| *F21W 131/202* | (2006.01) | |
| *F21W 131/205* | (2006.01) | |
| *F21Y 101/02* | (2006.01) | |

(52) U.S. Cl.
CPC .................. *E04B 9/006* (2013.01); *E04B 9/02* (2013.01); *F21S 2/005* (2013.01); *F21S 8/02* (2013.01); *F21S 8/033* (2013.01); *F21V 21/02* (2013.01); *F21V 21/15* (2013.01); *F21V 21/30* (2013.01); *F21V 33/006* (2013.01); *F21V 33/0088* (2013.01); *F21S 8/026* (2013.01); *H05B 33/0854* (2013.01); *H05B 37/0272* (2013.01); *A61B 2019/5255* (2013.01); *F21W 2131/202* (2013.01); *F21W 2131/205* (2013.01); *F21Y 2101/02* (2013.01)

USPC ....................................................... 362/147

(56) References Cited

U.S. PATENT DOCUMENTS

| 5,526,245 A | 6/1996 | Davis et al. | |
|---|---|---|---|
| 2011/0146676 A1* | 6/2011 | Dallam et al. ........... | 128/203.12 |

FOREIGN PATENT DOCUMENTS

| EP | 0422331 A2 | 4/1991 |
|---|---|---|
| EP | 1568935 A1 | 8/2005 |
| EP | 2060847 A1 | 5/2009 |
| WO | WO01/69130 A1 | 9/2001 |
| WO | W02007036581 A1 | 4/2007 |

OTHER PUBLICATIONS

Extended European Search Report Application No. 10171132.3-2423, issued by the European Patent Office, Munich, Germany dated May 30, 2011.
International Preliminary Report on Patentability, Application No. PCT/EP2011/062998 issued by The International Bureau of WIPO, Geneva, Switzerland, dated Jan. 29, 2013.
Written Opinion of the International Searching Authority, Application No. PCT/EP2011/062998 issued by the European Patent Office, Munich, Germany, dated Feb. 22, 2012 (note: this is the written opinion portion of NPL 1).

* cited by examiner

LAMP AND PLENUM FOR LAMINAR AIR FLOW CEILING

The present disclosure relates to a lamp for mounting on a part of a ceiling or a part of a wall, more particularly to a lamp which is particularly suitable for being mounted on a ceiling of an Operating Room (OR).

BACKGROUND

In order for a medical specialist and his/her team to be able to perform a surgical intervention, intensive illumination of an operation area and particularly a patient's inside is generally necessary.

To this end, many OR's are provided with lamps mounted on a distal end of movable supporting arms. These arms may be controlled manually in order to direct light in a desired direction and provide the proper illumination needed during the surgery.

This conventional way of illuminating an OR however has several disadvantages. For example, each of the lamps has to be manually manipulated to illuminate a particular area of an OR. If an operation requires various areas of a human body or various areas of an OR to be illuminated (apart from a patient e.g. also an instrument cart or table), this may be hard to achieve using these conventional means. Also, the areas of an OR that need to be illuminated may change during an operation, the various lamps may thus have to be continuously manipulated manually, which can be cumbersome. Furthermore, the presence of a supporting arm and a lamp may disturb the laminar air flow established by a Laminar Air Flow (LAF) ceiling; even more so if a plurality of lamps is provided in order to be able to illuminate different parts of an OR.

Laminar air flow ceilings may be provided in (parts) of operating rooms to establish a substantially laminar vertical air flow from the ceiling to an operating area. This air flow is provided to keep an operating area (and in particular the patient) free from germs, bacteria, pathogens etc. and avoid that the medical specialist and his/her support personnel contaminates the operating area of the patient.

The presence of the supporting arms and lamps may disturb the laminar air flow established by the LAF ceiling and thus may lead to a higher risk of infections occurring after an operation.

WO 2007/036581 discloses a lighting system including an array of light-emitting elements, in which the light-emitting elements can be individually controlled or in groups. This solves the problem of simultaneously illuminating different areas of an OR. However, the array of light-emitting elements is suspended from a ceiling and can significantly disturb the laminar air flow of an LAF ceiling.

WO 01/69130 discloses a ceiling having a plurality of prefabricated lighting module elements. Said lighting module elements include a gyroscopic suspension system in order to rotate a light bulb (or LED elements) around two axes. The gyroscopic suspension system however occupies a large space and requires a cumbersome installation. Moreover, if such a lamp is mounted in an LAF ceiling, the space occupied by the lamp cannot be used for passing air into the OR.

The present developments are aimed at avoiding or at least partially reducing one or more of the before-mentioned disadvantages related to prior systems. Further advantages will become apparent from the description that follows.

SUMMARY

In a first aspect, the present disclosure provides a lamp having a first module for being attached to a wall or ceiling element, a second module connected to the first module and being rotatable with respect to the first module along a first axis, a third module having one or more light-emitting elements, the third module being connected to the second module and rotatable with respect to the second module along a second axis, the second axis being substantially perpendicular to the first axis.

In this aspect hereof, a lamp is provided which is capable of widely varying the area it is illuminating (the lamp can be rotated around two perpendicular axes), while at the same time being easily mountable and only occupying a reduced space.

In some implementations, said first module has a first motor having a first output shaft with a first gearing, said first gearing meshing with gearing arranged on the second module. Using this arrangement, the first and second module can be arranged substantially along the same longitudinal axis, the lamp thus occupying less space.

Preferably, the second module has a mechanism for rotating the third module along said second axis, said mechanism substantially not protruding beyond the edges of the second module. In some of these implementations, the second module may have a second motor having a second output shaft with a first pivot mounted at or near its end, a first end of a first rod connected at a first end of said first pivot, and a first end of a second rod connected at a second end of said first pivot, the second end of said first rod connected to a first end of a second pivot, and the second end of said second rod connected to a second end of the second pivot, said second pivot being mounted on a third shaft arranged along said second axis, such that said third shaft can be rotated by said second motor. With this particular arrangement, the second module and third module may be arranged along the same longitudinal axis, whereas the third module rotates along an axis perpendicular to this line. This may further limit the space occupied by lamps according to the present disclosure.

In some implementations, the third module may have a plurality of LEDs. These LEDs may all be substantially the same, or different types of LEDs (e.g. different colours) may be provided within a single lamp. In alternative implementations, one or more light bulbs may be used.

In another aspect, the disclosure provides a laminar air flow ceiling for an operating room having a plenum, the plenum being defined by an upper horizontal wall, a lower horizontal wall, and four side walls and a plurality of lamps as substantially previously described. Preferably, said plurality of lamps is arranged substantially within said plenum. The lamps do not occupy a lot of space and can be arranged easily in the plenum. In this aspect, the laminar air flow from the LAF ceiling is not disturbed, while the lamps are still able to illuminate various parts of an operating room selectively.

In some implementations, the second axes of the plurality of lamps lie substantially in a plane coinciding with the lower horizontal wall of the plenum. In these implementations, the lamps do not substantially protrude beyond the plenum and thus cannot substantially disturb the laminar air flow. Simultaneously, any light produced by light-emitting elements in the third module of the lamps is not blocked by a part of the ceiling.

In some implementations, the first modules of the plurality of lamps are mounted at the upper horizontal wall of the plenum. In this aspect, the lamps may be mounted in a particularly easy manner.

In some implementations, a plurality of tubular elements is provided substantially within said plenum, each tubular element surrounding one of the lamps. Optionally, said tubular elements are mounted at a first end to the upper wall of the plenum, and are mounted at a second end to the lower wall of the plenum. A particularly easy way to mount the lamps is hereby provided. Additionally, a tubular element surrounding a lamp may avoid contamination of components of the lamp and may also reduce possible disturbance in the air flow within the plenum.

In some implementations, a lower wall of the plenum may have a plurality of rectangular lower wall elements. Such a modular built-up may be particularly easily manufactured and assembled.

Optionally, one or more of said lower wall segments may have a cut-out adapted to substantially fit a lamp as substantially hereinbefore described. Optionally, said cut-outs may be provided in corner areas of rectangular lower wall elements. In this aspect of the present disclosure, the area of the ceiling for passing the laminar air flow may be maximized.

BRIEF DESCRIPTION OF THE DRAWINGS

Particular implementations of the present disclosure will be described in the following, only by way of non-limiting examples, with reference to the appended drawings, in which.

DETAILED DESCRIPTION

Figure 1A:
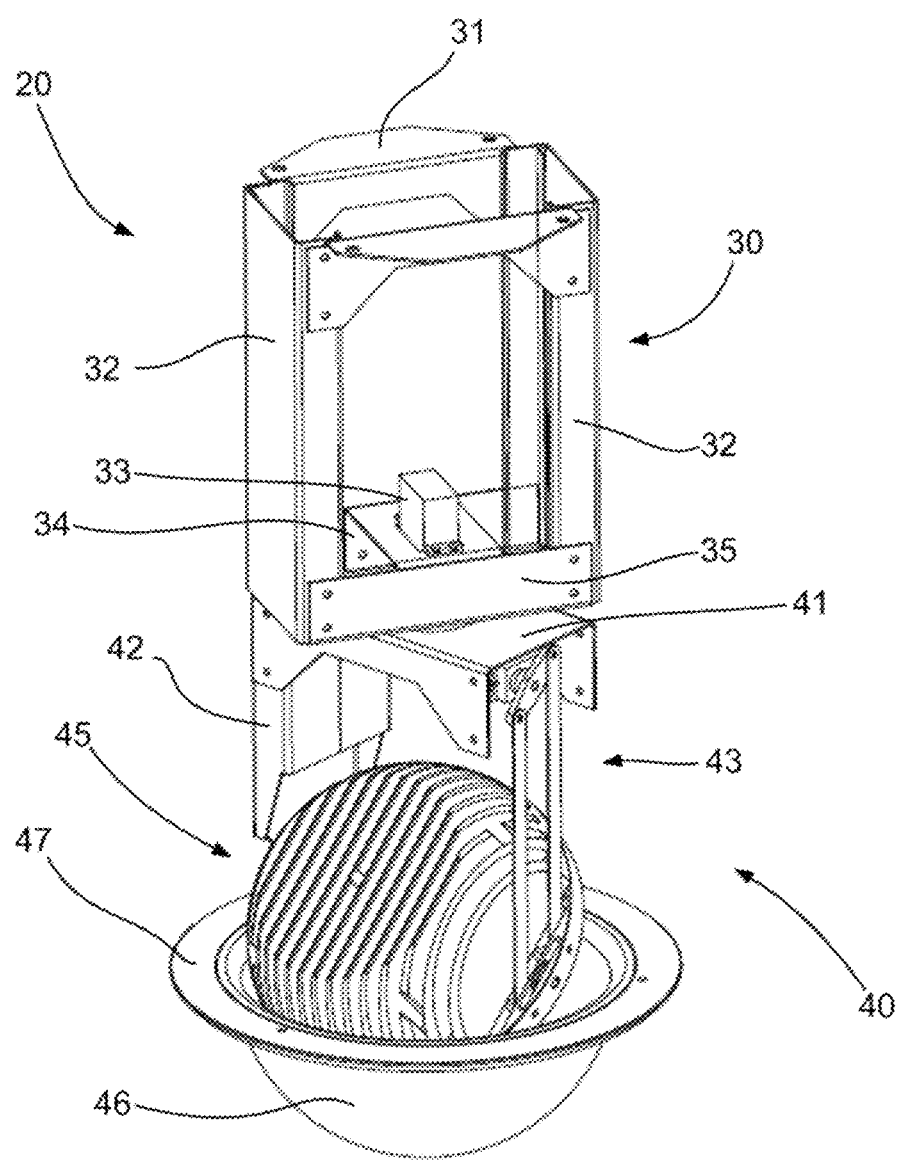
FIGS. 1a-1f illustrate a first implementation lamp according to the present disclosure.

FIG. 1a shows an isometric view of a partially cut-open lamp according to an implementation of the present disclosure. Lamp 20 includes a first module 30, a second module 40 and a third module 45. First module 30 has mounting brackets 31 for mounting the lamp to a part of a ceiling (or alternatively a part of a wall). Side brackets 32 connect mounting brackets 31 to bottom brackets 35. The brackets form the load-carrying frame of the first module. Suitable plate elements may be provided between the brackets to form a closed housing. A first motor base 34 is provided on the bottom brackets 35. A first motor 33 is connected to said first motor base 34.

In this implementation, second module 40 has a base bracket 43. From the sides of the base bracket 41, two side brackets 42 extend downwards (only one shown in FIG. 1a). Actuation mechanism 43 is provided to rotate third module 45 with respect to second module 40. A semi-spherical cover 46, which may be substantially transparent or translucent is provided and has an annular rim 47. Some more details of the lamp according to this first implementation may become apparent from FIGS. 1b-1f.

Figure 1B:
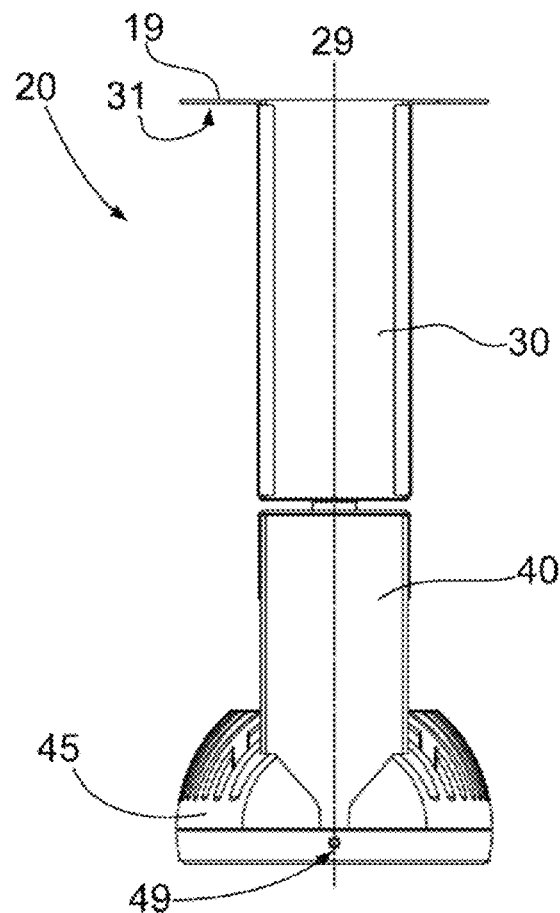

In FIG. 1b, reference sign 29 is used to indicate the axis 29 around which the second module 20 can rotate with respect to the first module 30. A ceiling or wall element 19 is shown to which mounting brackets 31 may be connected with any suitable fastening method (screws, bolts, welding, adhesives etc.). Also indicated is shaft 49 which constitutes the second axis around which the third module 45 can be rotated with respect to the second module 40. Shaft 49 is substantially perpendicular to axis 29. This gives the lamp a wide operational freedom, as is illustrated in FIG. 1e.

Figure 1C:
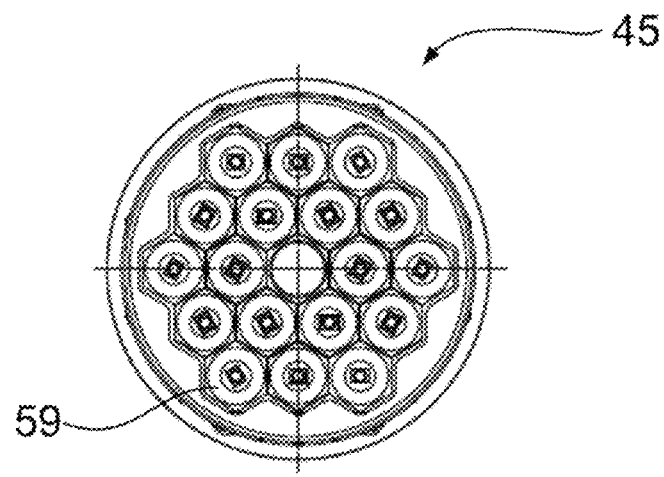
Figure 1D:
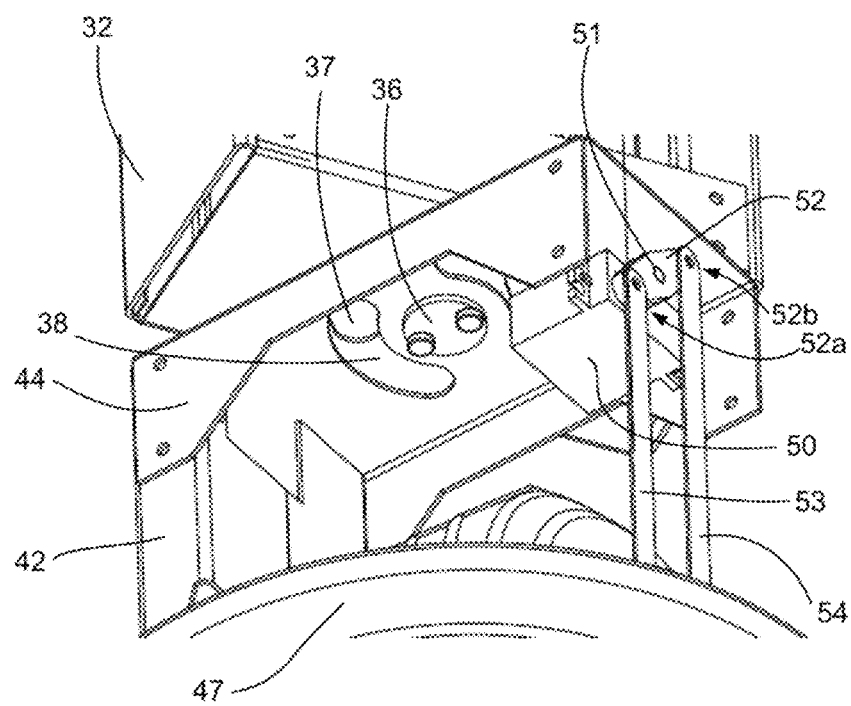
Figure 1E:
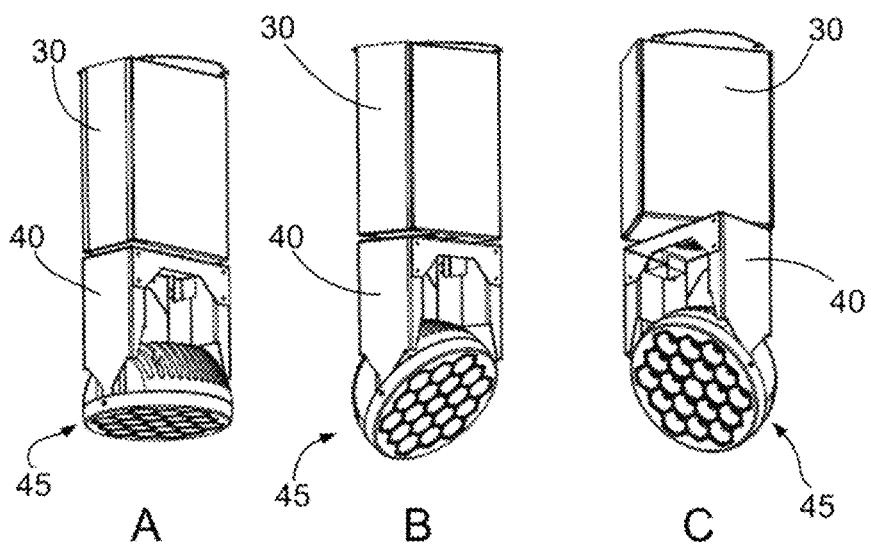

In situation A of FIG. 1e, a lamp is shown with both the second and the third module in a 0° position. In situation B, third module 45 has been rotated 45° with respect to the second module 40. In situation C, second module 40 has also been rotated 45° with respect to the first module 30. It is thus shown that using a lamp according to this implementation, due to the perpendicular arrangement of the two axes, a wide variation of illumination directions can be achieved with a single lamp.

FIG. 1e also illustrates the first and second modules with complete housings, i.e. including plate work between the various brackets. It can be seen in FIG. 1e that the mechanism for rotating the third module with respect to the second module does not protrude substantially beyond the edges of the second module, thus making the lamp compact. In the particular design of FIG. 1, when the second modules is at a 0° position with respect to the first module, the mechanism for rotating the third module does also not protrude beyond the imaginary extension of the edges of the first module.

FIG. 1d illustrates some details of the actuating mechanism of the first and second modules. The second module has a second motor 50 attached to base bracket 41. A pivot 52 is attached in an end region of the second motor's output shaft 51. At a first end 52a and at a second end 52b of pivot 52, a first and second rod 53 and 54 are mounted respectively. First and second rods 53 and 54 are connected at their other ends to a first and second end of a second pivot (see FIG. 1a). This second pivot is mounted on shaft 49, such that when second motor 50 is actuated, the first and second pivot rotate in unison to rotate third module 45 around shaft 49.

Base bracket 41 may have guides 38, in which bosses 37 of the first module are guided. Bearing disk 36 ensures the connection between the first module and second module. Not shown in FIG. 1d is a gearing of the second module meshing with a gearing arranged on the output shaft of first motor 33.

Figure 1F:
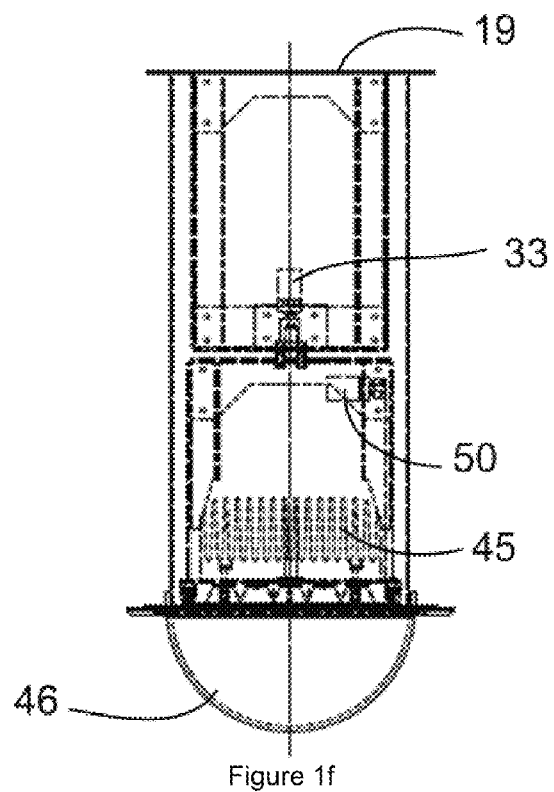

FIG. 1f provides a different view of the same actuation mechanisms. The same figure also highlights cooling slits of third module 45 and semi-spherical cover 46.

Finally, FIG. 1c shows a plurality of light-emitting elements 59 arranged in third module 45. In this particular implementation, 18 LEDs are provided. It will be clear however, that any different number of LEDs may also be used. Additionally, instead of LEDS, other light-emitting elements (such as e.g. light bulbs) may also be used. LEDs however may present some advantages over incandescent light sources including lower energy consumption, longer lifetime, smaller size, and greater reliability.

In the implementation shown, the modules were composed of load-carrying brackets and substantially non-load-carrying plate work. It will be clear however that many other possible structures may be provided within the scope of the disclosure.

Figure 2A:
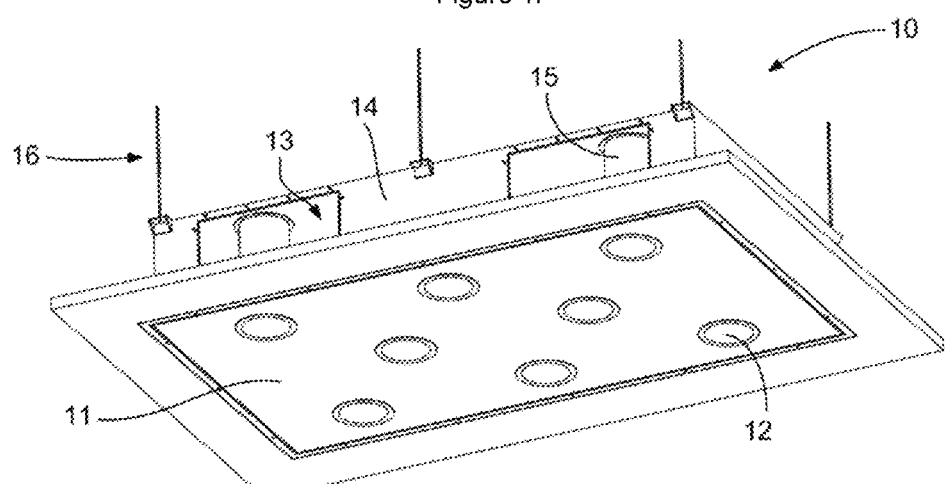
FIGS. 2a-2c illustrate an implementation of a lamp according to the present disclosure mounted in an LAF ceiling arrangement.
Figure 2B:
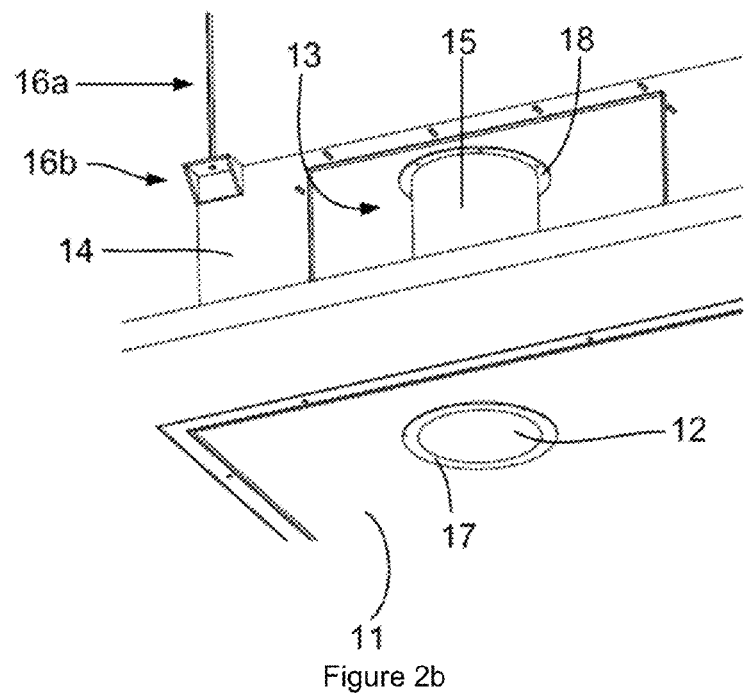

The power needed for the first and second motor and for the light-emitting elements may be provided through electrical wiring and a connection to the electrical grid. Alternatively, independent power sources such as batteries may also be used. FIGS. 2a-2b illustrate an implementation of a lamp according to the present disclosure mounted in an LAF ceiling arrangement. The LAF ceiling has been indicated with reference sign 10. In this implementation, the LAF ceiling 10 is suspended from an OR ceiling with a plurality of cables 16 and attachments 16b (see FIG. 2b). In alternative implementations, the LAF ceiling 10 may also be integrated in the OR ceiling itself. In yet further implementations, the LAF assembly may be arranged in a sidewall of a room. Such arrangements may be useful in other applications of the present disclosure.

LAF ceiling may include a plenum 13 delimited by an upper wall 19, a lower wall 11 and four side walls 14. A laminar air flow may be established by an under pressure in the OR with respect to the plenum. A large number of small straight vertical holes is provided in bottom wall 11, through which the air can pass. Air is also sucked out of the OR (e.g. through a ventilation hole in a side-wall), filtered and re-supplied to the plenum 13. A plurality of lamps 12 is mounted substantially in the plenum. Each of the lamps is provided in a substantially cylindrical tube 15.

In this implementation, the cylindrical tube extends from the upper wall to the bottom wall of the plenum and does not substantially extend into the area directly below the LAF ceiling and thus cannot disturb any laminar air flow in that area. At the upper wall, tube 15 is mounted at a rim 18 and at the lower wall 11, tube 15 is mounted with rim 17.

An advantage of the arrangement shown is that the plurality of lamps can be easily mounted with respect to the plenum. Also it can be seen that the lamps do not have supports or mechanisms occupying space in the plenum or interfering with the flow in the plenum. It will be clear however, that while maintaining a modular built-up and easy assembly, different cross-sectional shapes may be chosen for the tubular element 15.

Figure 2C:
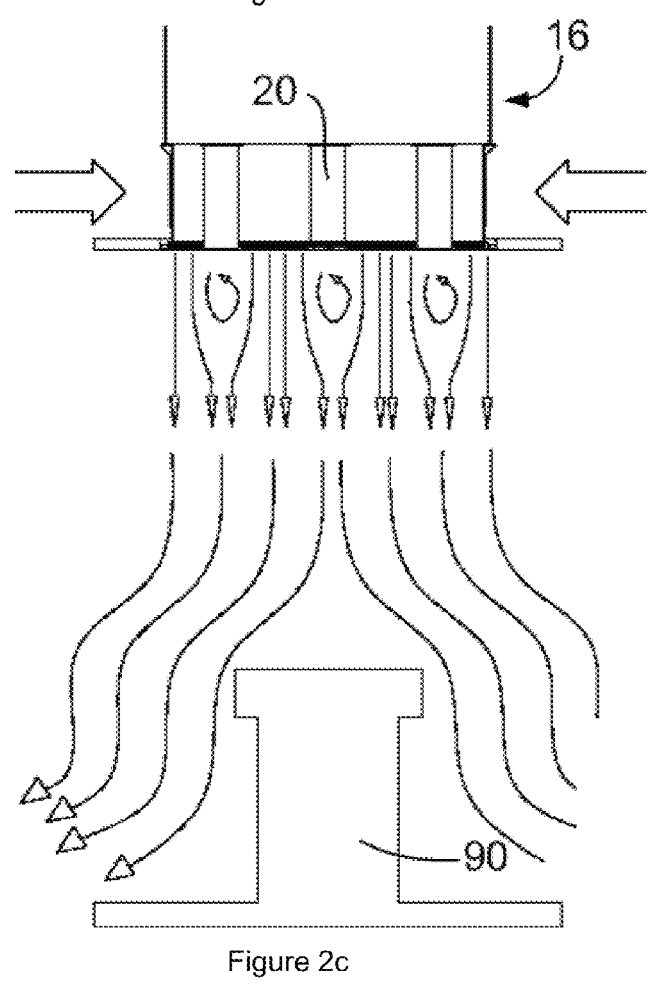

FIG. 2c schematically illustrates the air flow that may be generated using an LAF ceiling and a plurality of lamps according to the present disclosure. The side walls of the plenums have openings allowing air to enter into the plenum. Immediately below the LAF ceiling, the air flow may still be somewhat turbulent. But a short distance below the LAF ceiling, a laminar air flow establishes itself, which is not further disturbed by an illumination system. Also illustrated in FIG. 2c is how such a laminar air flow may keep the operating are, on top of operating table 90 substantially free from bacteria, germs etc.

Figure 3:
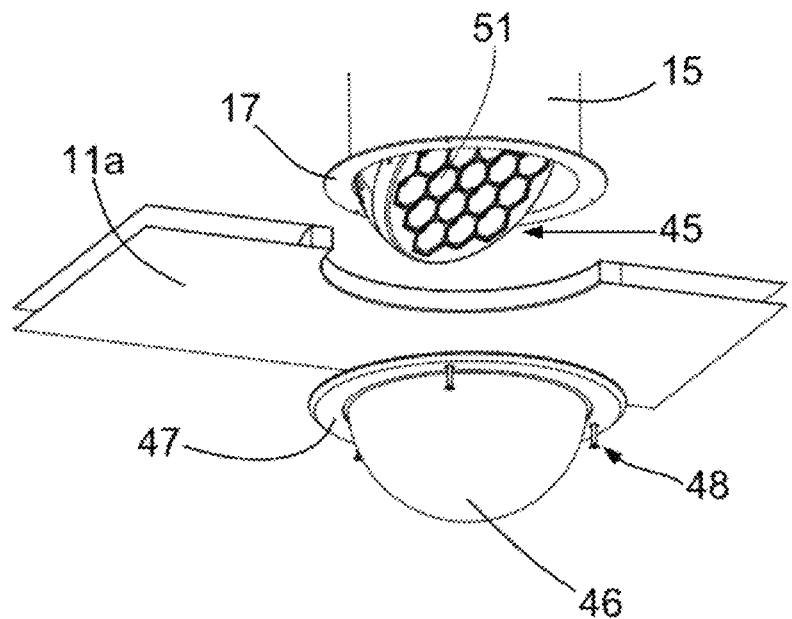
FIG. 3 illustrates a detail of an implementation of a lamp according to the present disclosure.

FIG. 3 shows a similar lamp in a cylindrical tube 15. At its lower rim 17 it may be connected through a plurality of e.g. bolts or screws to a bottom wall element 11a of a LAF ceiling plenum. It can be seen that in such an assembled state, the second axis of the second module (around which the third module rotates) may substantially coincide with lower wall 11.

Semi-spherical cover 46 is connected to the wall element 11a using screws 48. In other implementations, other shapes than semi-spherical may be chosen for the cover. An advantage of the semi-spherical cover is particularly that regardless of the orientation of the third module 45, the light falls perpendicularly onto the cover and thus can pass through it. Another advantage is that the semi-spherical cover promotes a laminar air flow. It will be clear however that also with other shapes, a laminar air flow may be established while also allowing sufficient light to pass.

Figure 4:
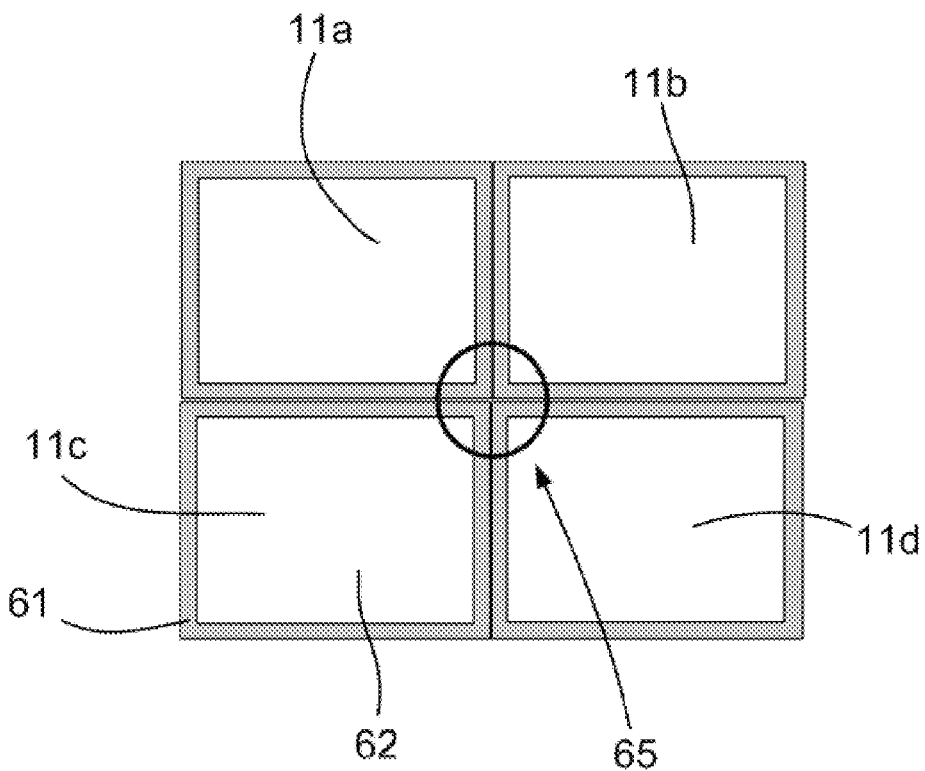
FIG. 4 illustrates a possible lay-out of an LAF ceiling which may be advantageously used in combination with implementations of lamps according to the present disclosure.

FIG. 4 illustrates a section of a lower wall 11 of an LAF ceiling having segments 11a, 11b, 11c and 11d. The lower wall 11 in this implementation thus also has a modular built-up. In a preferred implementation, all elements have a quarter circular cut-out, so that four elements together form a substantially circular hole, in which a lamp may be fitted.

Each of the elements 11a-11d has a central area 62 and an edge area 61. In the edge area, the density of holes to establish the laminar air flow will be lower than in the central area 62. Providing a cut-out in a corner thus allows maintaining a higher laminar air flow capacity. Alternatively, a cut-out may be made in a different part of the edge area (not in a corner).

In some implementations, lamps may even be fitted in a central area of a ceiling segment.

It will further be clear that it is not necessary for four quarter circular cut-outs to together form a circular cut-out. Depending on the arrangement of the panels, e.g. two semi-circular cut-outs may also be used. It will also be clear that if a different shape is chosen for a tubular element, a different shape may be chosen for the cut-outs as well. Furthermore, it will be clear that different sizes and shapes (e.g. square) may be chosen for the ceiling segments.

In further implementations, more than one lamp may be provided in a single ceiling segment.

Figure 5:
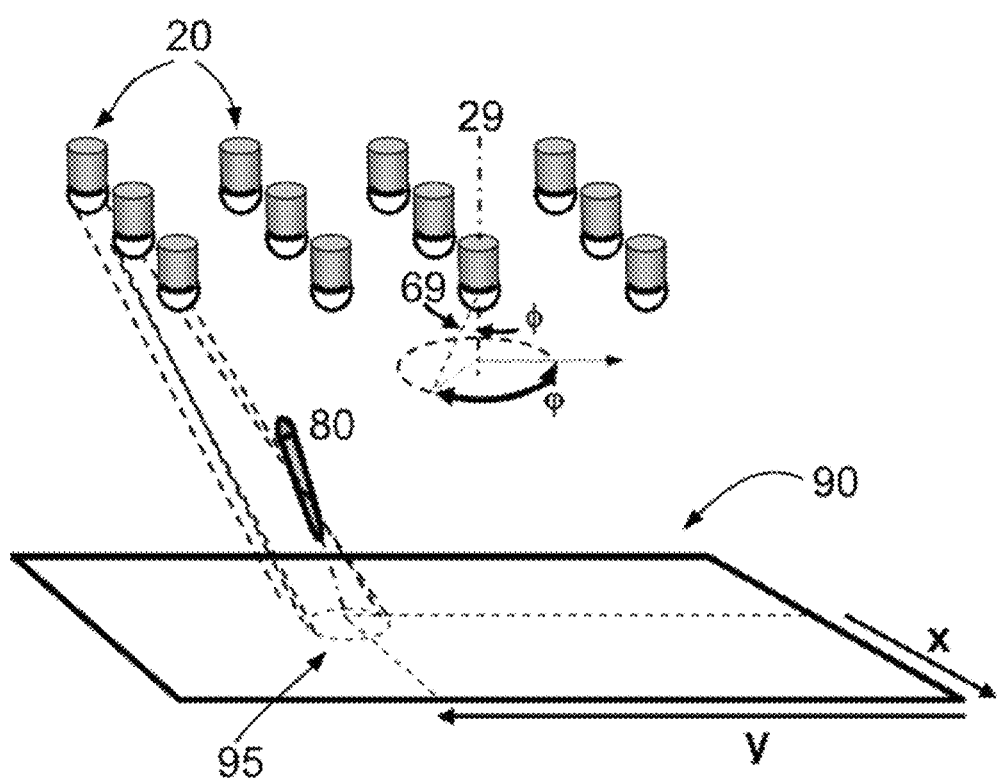
FIG. 5 schematically illustrates a method of illuminating an operating area of an OR using lamps according to the present disclosure.

A possible method of illuminating an operating area is illustrated with reference to FIG. 5. A plurality of lamps 20 arranged on a ceiling of an OR is shown. Each of the lamps 20 may be individually controlled. The lamps 20 may be rotated along two perpendicular axes: along a first axis 29 to determine angle $\phi$, and along a second axis 69 (not shown) to determine angle $\Phi$.

Using a pointer 80, a surgeon or his/her support team may indicate which specific area 95 of the operating table 90 should be illuminated. To this end, both extremes of pointer 80 may have e.g. an infrared-emitter which may be detected by one or more of a plurality of video cameras that may be arranged along the walls and ceiling of the OR.

If the IR-emitters are detected by at least three cameras, their three-dimensional position may be determined exactly. In preferred implementations, at least four cameras are provided, so that even if one camera is temporarily visually blocked (for example by personnel operating in the OR) from registering one of the IR-emitters, its position can still be reliably detected. By detecting both positions of the IR-emitters, not only the position of the pointer may be determined, but also its orientation. This way, the control system may know which area is to be illuminated, and also from which direction. This may avoid light not reaching the desired area because of shadows created by personnel or other obstacles.

Using the plurality of lamps, separate areas of the OR may be conveniently illuminated. In some implementations, some lamps may assume different default positions. This way, even with limited rotational movement, blind spots in the OR may be avoided. Also, in some implementations, different lamps may have different light-emitting elements, such that a suitable lamp may be selected for different illumination "tasks".

In preferred implementations, controls are integrated in the pointers that e.g. allow the intensity of the light to be regulated, and/or allow the size of the illuminated are to be regulated. This aspect may be used to be able to regulate the light for a particular purpose: a higher intensity of light of a small area may be needed for illuminating a surgical entry point in a patient's body than for e.g. illuminating an instrument cart (for which a larger area may need to be illuminated with a lower light intensity). In further implementations, LEDs within one lamp 20 may be controlled individually or in groups.

It will be clear however that many alternative methods of control may be used in combination with implementations of the disclosure. In alternative implementations, the control of the plurality of lamps may be automatic or semi-automatic: using suitable sensors, the areas to be illuminated may be detected and the lamps may be controlled accordingly.

Although this disclosure was described with particular reference to an Operating Room, it will be clear that the lamp according to the disclosure may have other applications. In particular, the lamp according to the disclosure may also be advantageously used e.g. in dentists' treatment rooms, veterinary operation areas and clean rooms.

Although this disclosure has been disclosed in the context of certain preferred implementations and examples, it will be understood by those skilled in the art that the present disclosure extends beyond the specifically disclosed implementations to other alternative implementations and/or uses of the disclosure and obvious modifications and equivalents thereof. Thus, it is intended that the scope of the present disclosure herein disclosed should not be limited by the particular disclosed implementations described before, but should be determined only by a fair reading of the claims that follow.

The invention claimed is:

1. A laminar air flow ceiling for an operating room comprising: a plenum providing a laminar air flow for the laminar air flow ceiling, the plenum defined by an upper horizontal wall, a lower horizontal wall, and one or more side walls, and a plurality of lamps arranged substantially within said plenum, wherein the lamps comprise: a first module; a second module connected to the first module and being rotatable with respect to the first module along a first axis; a third module comprising one or more light-emitting elements, the third module being connected to the second module and rotatable with respect to the second module along a second axis; the second axis being substantially perpendicular to the first axis; wherein the second module of the lamps comprises a mechanism for rotating the third module along said second axis, said mechanism substantially not protruding beyond the edges of the second module, wherein said second module of the lamps comprises a second motor having a second output shaft with a first pivot mounted at or near its end, a first end of a first rod connected at a first end of said first pivot, and a first end of a second rod connected at a second end of said first pivot, the second end of said first rod connected to a first end of a second pivot, and the second end of said second rod connected to a second end of the second pivot, said second pivot being mounted on a third shaft arranged along said second axis, such that said third shaft can be rotated by said second motor;
The plenum and plurality of lamps configured to maintain laminar air flow.

2. A laminar air flow ceiling according to claim 1, wherein the second axes of the plurality of lamps lie substantially in a plane coinciding with the lower horizontal wall of the plenum.

3. A laminar air flow ceiling according to claim 1, wherein the first modules of the plurality of lamps are mounted at the upper horizontal wall of the plenum.

4. A laminar air flow ceiling according to claim 1, wherein a plurality of tubular elements are provided substantially within said plenum, each tubular element surrounding one of the lamps.

5. A laminar air flow ceiling according to claim 4, wherein said tubular elements are mounted at a first end to the upper wall of the plenum, and are mounted at a second end to the lower wall of the plenum.

6. A laminar air low ceiling according to claim 1, wherein said lower wall of the plenum comprises a plurality of rectangular lower wall elements.

7. A laminar air low ceiling according to claim 6, wherein one or more of said lower wall segments comprise a cut-out adapted to substantially fit one of the lamps.

8. A laminar air flow ceiling according to claim 7, wherein said cut-out is provided in a corner area of a rectangular lower wall element.

9. A laminar air low ceiling according to claim 1, wherein each of said plurality of lamps comprises a substantially semi-spherical cover.

10. A laminar air flow ceiling according to claim 1, wherein said first axis of the lamps is an axis perpendicular to the upper wall.

11. A laminar air flow ceiling according to claim 1, wherein said first module of the lamps comprises a first motor having a first output shaft with a first gearing,
    said first gearing meshing with gearing arranged on the second module.

12. A laminar air flow ceiling according to claim 1, wherein said third module comprises a plurality of LEDs.

* * * * *